United States Patent [19]
Barrow et al.

[11] Patent Number: 5,512,304
[45] Date of Patent: * Apr. 30, 1996

[54] METHOD OF PREPARING A THROMBOPLASTIN EXTRACT

[75] Inventors: David A. Barrow, Sour Lake; Richard L. Rullman, Beaumont, both of Tex.

[73] Assignee: Helena Laboratories Corporation, Beaumont, Tex.

[ * ] Notice: The portion of the term of this patent subsequent to Jul. 22, 2011, has been disclaimed.

[21] Appl. No.: 383,370

[22] Filed: Feb. 3, 1995

Related U.S. Application Data

[60] Continuation of Ser. No. 60,980, May 14, 1993, Pat. No. 5,391,380, which is a division of Ser. No. 733,325, Jul. 22, 1991, Pat. No. 5,254,350.

[51] Int. Cl.$^6$ .................................................... A61K 35/30
[52] U.S. Cl. .............................. 424/570; 424/583; 514/2; 514/21; 530/381; 435/13
[58] Field of Search ..................................... 424/570, 583; 514/2, 21; 530/381; 435/13

[56] References Cited

U.S. PATENT DOCUMENTS

| | | |
|---|---|---|
| 3,522,148 | 7/1970 | Adam et al. ................................ 435/13 |
| 4,416,812 | 11/1983 | Becker et al. .......................... 435/212 |
| 4,784,944 | 11/1988 | Kolde ........................................ 435/13 |

FOREIGN PATENT DOCUMENTS

WO9005740  5/1990  WIPO .

OTHER PUBLICATIONS

Hubbard et al., "Inhibition of Tissue Thromboplastin-Mediated Blood Coagulation," *Thrombosis Research* 42: 489–498 (1986).

Pawashe et al., "Molecular Cloning, Characterization and Expression of cDNA For Rabbit Brain Tissue Factor", Thrombosis & Haemostasis, 66 (3) 315–320 (1991).

Biochem. Methods, vol. 116, 1992, "Recombinant Tissue Factor as Substitute for Conventional Thromboplastin in the Prothrombin Time Test", Tripodi et al.

Hubbard et al., Biol. Abstr., 82(3):AB–85, Blood, Organs and Body Fluids, Ref. No. 20346.

Jensen et al., "Tissue Factor Pathway Inhibitor", Clinical Hemostasis Review, vol. 6, No. 6, Jun. 1992.

Pharmaceuticals, vol. 110, 1989, "Sorbent for Extracting and Purifying Thromboplastin and Method of Producing Same", Staroverov et al.

"Gel Chromatography of High–Molecular–Weight Complexes of Thromboplastin", Fadeeva et al.

"Partial Purification of Tissue Thromboplastin by means of Gel Filtration and Reproduction of the Syndrome . . . Thrombinogenesis . . . ", Magerovskii et al.

*Primary Examiner*—Marian C. Knode
*Assistant Examiner*—Jean C. Witz
*Attorney, Agent, or Firm*—Dorsey & Whitney

[57] ABSTRACT

A thromboplastin extract including an aqueous thromboplastin extract of a powdered thromboplastin source including a metal ion chelator. A thromboplastin reagent for use in blood coagulation tests, the thromboplastin reagent includes the extract and calcium ions, and may include one or more of a stabilizer and a preservative.

A process for preparing a thromboplastin extract including extracting a powdered thromboplastin source in an aqueous solution having a metal ion chelator, and separating the powder in solution into sedimented powder and supernatant thromboplastin extract. The supernatant thromboplastin extract is mixed with calcium ions, and may be mixed with one or more of a stabilizer and a preservative, to prepare thromboplastin reagent.

12 Claims, No Drawings

METHOD OF PREPARING A THROMBOPLASTIN EXTRACT

This is a continuation of application Ser. No. 08/060,980 filed May 14, 1993, now U.S. Pat. No. 5,397,380, which is a divisional of application Ser. No. 07/733,325, filed Jul. 22, 1991, now issued as U.S. Pat. No. 5,254,350.

BACKGROUND OF THE INVENTION

1. Field of the Invention

This invention relates to thromboplastin extracts and reagents, and more particularly to thromboplastin extracts and reagents including a chelator.

2. Technology Background

Blood coagulation involves a succession of reactions leading to the formation of fibrin. Fibrin is the protein that holds blood clots together. Fibrin is formed from a soluble precursor, fibrinogen, by the protease thrombin. Thrombin is generated during clotting from an inactive precursor, prothrombin (Factor II), through one of two mechanisms known as the extrinsic and intrinsic pathways. The extrinsic pathway comes into action in response to tissue injury, and involves the participation of blood clotting factors V, VII, and X. The extrinsic and intrinsic pathways converge in a final common pathway for the thrombin-catalyzed conversion of fibrinogen to the fibrin clot.

Clinical tests of blood coagulation include the prothrombin time test. The prothrombin time test is a measure of the extrinsic pathway of blood coagulation. Prothrombin time, hereinafter (PT), measures the time elapsing until plasma clots in the presence of a tissue thromboplastin reagent. The test is performed by adding a tissue thromboplastin reagent to the plasma and determining the time necessary for coagulation. The thromboplastin reagent, along with factor VII, activates factor X to $X_a$ (active factor X) in the presence of factor $V_a$ (active factor V), $Ca^{2+}$, and platelet phospholipids. Prothrombin is converted to thrombin, which in turn catalyzes the formation of fibrin from fibrinogen. Thus, a deficiency of factor II, V, VII, or X or a severe deficiency of fibrinogen will prolong the PT. Normal plasma contains factors VII and X; therefore, if normal plasma corrects the PT, the defect must be due to a deficiency of one of those two factors.

Blood coagulation requires calcium. Since calcium is present in plasma itself, anticoagulants such as sodium citrate or EDTA are often placed in the vials that hold plasma to block its spontaneous coagulation. The plasma together with sodium citrate or EDTA as an anticoagulant is referred to as anticoagulated plasma. Calcium ions in a saturating amount are added according to the prior art to overcome the sodium citrate or EDTA and to prevent the sodium citrate or EDTA from affecting PT time.

The prothrombin time test can monitor coumarin therapy for maintenance of the therapeutic range. The coumarin drugs are used clinically to impede blood coagulation in thrombotic states, including heart disease. They inhibit the vitamin K-dependent synthesis of factors II, VII, IX and X.

U.S. Pat. No. 3,522,148, dated Jul. 28, 1970, to Adam, Jr. discloses a stabilized thromboplastin reagent including a mixture of a saline extract of acetone-dried rabbit brain tissue and a sodium salt, and an equal volume of aqueous solution of calcium chloride. Adam, Jr. also discloses a stabilized thromboplastin reagent including a mixture of a saline extract of acetone-dried rabbit brain tissue and an equal volume of a calcium salt of a sugar acid. U.S. Pat. No. 4,784,944, dated Nov. 15, 1988, to Kolde, H. J. discloses thromboplastin obtained from human placenta.

The three general steps in preparing a thromboplastin reagent include preparing a powdered thromboplastin source, converting the powdered thromboplastin source into a thromboplastin extract, and preparing a useful thromboplastin reagent from the thromboplastin extract.

Sources of thromboplastin include rabbit brain, human placenta, bovine brain, ox brain, human brain, and thromboplastin produced by recombinant DNA technology. Powdered thromboplastin sources include rabbit brain powder, powdered human placenta, powdered bovine brain, powdered ox brain, powdered human brain, and powdered thromboplastin produced by recombinant DNA technology.

Rabbit brain powder is prepared according to the prior art by homogenizing whole rabbit brains stripped of attached blood vessels with excess acetone, and drying the slurry under vacuum. Rabbit brain powder is commercially available.

Powdered human placenta is prepared according to the prior art in a manner similar to the preparation of rabbit brain powder.

Rabbit brain powder is converted into a useful thromboplastin extract according to the prior art by a procedure that involves extraction of the powder in warm saline solution and centrifugation to remove the sedimented brain powder, leaving a supernatant extract rich in thromboplastin. U.S. Pat. No. 4,416,812, dated Nov. 22, 1983, to Becker et al. discloses using calcium ions during extraction.

The thromboplastin reagent is then prepared from the extract by combining the extract with stabilizers and preservatives and one of various calcium salts to produce a bulk reagent, and then usually lyophilizing the reagent for long-term storage.

A problem which limits the effectiveness of the prothrombin time test is that chemical variation of the thromboplastin extract and the thromboplastin reagent formulations can alter the PT. The PT for normal human plasma based on the use of fresh basic raw material, rabbit brain powder, is the standard value for comparison. Physicians in the United States relying on PT results for screening and diagnostic purposes generally expect normal human plasma to clot within 12 seconds after contact with a standardized thromboplastin reagent that is lyophilized and reconstituted. The in-process extract solutions before lyophilization and reconstitution into a standardized thromboplastin reagent are required to provide a PT of less than or equal to 11 seconds. From time to time, for as yet unknown reasons, rabbit brain powder from commercial suppliers may vary from its normal quality, and produce extracts unsuitable for reagent preparation by conventional methods because they yield long PTs for normal human plasma.

One way to accomplish standardized results of the prothrombin time test is to provide extracts and reagents that have a consistently lower PT of normal human plasma from lot to lot. Another way to achieve comparability is standardization in reference to a particular factor sensitivity. "Sensitive" reagents need not provide a lower PT value. However, it is beneficial for even so-called "sensitive" reagents to provide a lower PT value so that the effects of the variables that are modified to achieve a particular factor sensitivity do not prolong the reagent's PT of normal human to so great an extent that testing becomes impractical with automated instrumentation.

Accordingly, it is the main object of the present invention to provide a process for preparing a thromboplastin extract and reagent which overcomes the aforementioned disadvantages. Specifically, it is a principal object of this invention to provide extract and a thromboplastin reagent that consistently provides a lower PT of normal human plasma from lot to lot.

Another object of the invention is to improve a wide variety of powdered thromboplastin sources within a species such as rabbit brain powders all to a standard level of PT, thus allowing for improved lot-to-lot thromboplastin reagent reproducibility, so that data can be compared for meaningful, consistent results.

Another object of the invention is to provide a thromboplastin reagent from a raw powdered thromboplastin source such as rabbit brain powder that may not otherwise be useful for preparing a standardized thromboplastin reagent.

These objects and others which will become apparent as the specification progresses are accomplished by the invention.

SUMMARY OF THE INVENTION

The present invention provides a process for preparing a thromboplastin extract from a thromboplastin source by providing a powdered thromboplastin source, extracting said powdered thromboplastin source in an aqueous solution comprising a metal ion chelator, separating the powdered thromboplastin source in aqueous solution into sedimented powder and supernatant thromboplastin extract having the thromboplastin and isolating the supernatant thromboplastin extract. The process may further include freeze drying the supernatant thromboplastin extract. The supernatant thromboplastin extract prepared by this process may further include the metal ion chelator, or the metal ion chelator may precipitate. The thromboplastin source may be rabbit brain tissue or human placenta, for example, and the powdered thromboplastin source may be rabbit brain powder or powdered human placenta, for example.

The present invention provides a process for preparing a thromboplastin reagent by mixing the supernatant thromboplastin extract prepared by the above process with calcium ions. One or more of a stabilizer and a preservative may be added to the extract. The thromboplastin reagent produced by this process may but need not contain the metal ion chelator.

The present invention further provides a process for preparing a thromboplastin reagent comprising an aqueous thromboplastin extract of a powdered thromboplastin source including a metal ion chelator, and calcium ions by mixing a thromboplastin extract including an aqueous thromboplastin source and a metal ion chelator, with calcium ions. One or more of a stabilizer and a preservative may be added to the extract.

The present invention further provides a thromboplastin extract including an aqueous thromboplastin extract of a powdered thromboplastin source and a metal ion chelator. The present invention also provides a thromboplastin reagent including an aqueous thromboplastin extract of a powdered thromboplastin source and a metal ion chelator, and calcium ions, and may further include one or more of a stabilizer and a preservative.

DETAILED DESCRIPTION OF THE INVENTION

All original sources of thromboplastin may be used. Examples of sources of thromboplastin are human placenta, rabbit brain, bovine brain, ox brain, and human brain. Thromboplastin produced by recombinant DNA technology may be used. Preferably, the source of thromboplastin is rabbit brain.

Rabbit brain powder is commercially available and it may be isolated according to a standard technique by removing whole brains stripped of attached blood vessels from, for example, New Zealand White rabbits, homogenizing the rabbit whole brains in excess acetone in a Waring blender to produce a slurry, and drying the slurry under vacuum to produce rabbit brain powder which is stable when stored under vacuum at −20° C.

Powdered bovine brain, powdered ox brain, powdered human brain, powdered thromboplastin produced by recombinant DNA technology, and powdered human placenta are prepared in a manner according to the prior art similar to the preparation of rabbit brain powder.

The powdered thromboplastin source such as rabbit brain powder or human placenta powder is then extracted in an aqueous solution to prepare thromboplastin extract. The aqueous solution may be a warm saline solution. To solve the problem of lot-to-lot variations in PT time of normal plasma, the inventors have discovered that a metal ion chelator should be added during the extraction. According to the invention, the thromboplastin extract is prepared by extracting the powdered thromboplastin source in an aqueous solution including a metal ion chelator, separating the powdered thromboplastin source into sedimented powder and supernatant thromboplastin extract having thromboplastin, and isolating the supernatant thromboplastin extract. The separating step may be by centrifuging. The thromboplastin extract may then be freeze dried. The supernatant thromboplastin extract made by this process comprises an aqueous thromboplastin extract of rabbit brain powder or other source of thromboplastin such as human placenta powder, and it may further include a metal ion chelator. Alternately, the metal ion may precipitate and the extract does not include the metal ion chelator.

Any metal ion chelator that functions similarly to ethylenediaminetetraacetic acid (EDTA) in binding/chelation of calcium ions or other metal ions may be used for practicing the invention. Specific examples of metal ion chelators that may be used in the present invention are citrate, salts of citrate, EGTA (Ethylenebis(oxyethylenenitrilo)] tetraacetic acid, and salts of EGTA. Preferably, the metal ion chelator is ethylenediaminetetraacetic acid (EDTA) or a salt of EDTA. According to the invention, during extraction of a powdered thromboplastin source, a small amount of metal ion chelator is included. Approximately at least 0.1 mM of metal ion chelator is added to the aqueous solution of the extraction. Preferably, 0.5–5.0 mM of metal ion chelator is added to the aqueous solution. Most preferably, 1.0 mM of metal ion chelator is added to the aqueous solution. The metal ion chelator stock solution may be pH neutralized according to common laboratory practice. Preferably, a small amount of pH neutralized, concentrated metal ion chelator is delivered to the extraction solution prior to adding the powdered source of thromboplastin.

The thromboplastin reagent may then be prepared according to the invention by mixing the thromboplastin extract prepared by the above process with calcium ions. The thromboplastin reagent prepared by this process may but need not include the metal ion chelator in the final reagent.

The present invention further provides a process for preparing a thromboplastin reagent comprising an aqueous thromboplastin extract of a powdered thromboplastin source including a metal ion chelator, and calcium ions by mixing a thromboplastin extract including an aqueous thromboplastin source and a metal ion chelator, with calcium ions. One or more of a stabilizer and a preservative may be added to the extract.

Any source of calcium ions may be used for practicing the invention. Specifically, a calcium salt such as calcium chloride may be used. Calcium salts of sugar acids such as calcium tartrate, calcium gluconate, calcium citrate, or calcium lactate may be substituted for calcium chloride.

The thromboplastin extract according to the invention comprises an aqueous thromboplastin extract of a powdered thromboplastin source and a metal ion chelator.

The thromboplastin reagent according to the invention comprises a thromboplastin extract of rabbit brain powder or other source of a powdered thromboplastin source and a metal ion chelator, and calcium ions. The thromboplastin reagent contains calcium ions at a concentration of 5–20 mM, preferably 12 mM.

The thromboplastin reagent may contain a metal ion chelator if calcium ions are present in sufficient concentration to overcome the metal ion chelator level in addition to the amount of sodium citrate or EDTA present in the anticoagulated plasma. Calcium ions in a saturating amount are added to overcome the metal ion chelator, and the sodium citrate or EDTA, present in the anticoagulated plasma.

The thromboplastin reagent may further include a stabilizer. Any stabilizer that functions to maintain the activity of the thromboplastin reagent may be used for practicing the invention. Specifically, a buffer salt such as a Good buffer, or Tris (trishydroxymethylaminomethane) may be used. The stabilizer may be, for example, PIPES (Piperazine-N,N-bis (2-ethane-sulfonic acid, 1.5 sodium salt)); Imidazole; MOPSO (3-(N-Morpholino)-2-hydroxypropanesulfonic acid); BES (N,N-bis-(Hydroxyethyl)-2-aminoethanesulfonic acid); MOPS (3-(N-Morpholino) propanesulfonic acid); TES (N-tris-(Hydroxymethyl)-methyl-2-aminoethanesulfonic acid); HEPES (N-2-Hydroxyethyl piperazine-N-2-ethanesulfonic acid); DIPSO (3-[N-Bis(hydroxyethyl)amino] -2-hydroxypropanesulfonic acid); TAPSO (3-[N-tris(Hydroxymethyl)methylamino]-2-hydroxypropanesulfonic acid); POPSO (Piperazine-N,N'-bis(2 -hydroxy-propanesulfonic acid) ); HEPPSO (N-Hydroxyethyl piperazine-N'-2-hydroxypropanesulfonic acid); Tricine (N-Tris [hydroxymethyl]methyl-glycine); Bicine (N,N'-Bis-(2-hydroxyethyl)-glycine); and TAPS (3-[N-tris-(Hydroxymethyl) methylamino]-propanesulfonic acid).

The thromboplastin reagent may further include a preservative. Any preservative that functions to prevent the growth of microorganisms that would damage the thromboplastin reagent may be used for practicing the invention, such as antibacterial and antifungal compositions. Specifically, sodium azide, thimerosal, BHA, and BHT may be used. Preferably the preservative is thimerosal.

While not wishing to be bound by any theory, Applicants believe that the mechanism of their invention involves the known biochemical inhibitor of the Factor X activator complex called the Extrinsic Pathway Inhibitor (EPI). The inhibitory binding of EPI is mediated by calcium ions and can be reversed by chelators, such as EDTA or similar metal ion chelators. Break up of this EPI complex by chelators appears to allow isolation of thromboplastin free from the inhibitory EPI, assuming that the EPI partitions into the pelleted rabbit brain residue upon separation, for example, centrifugation. This latter assumption is reasonable since EPI is also known as lipoprotein associated coagulation inhibitor (LACI).

The following examples are offered by way of illustration and not by way of limitation.

EXAMPLE 1

A thromboplastin reagent was prepared from commercially available rabbit brain powder according to the invention as follows:

A 10.0 g amount of rabbit brain powder was extracted using a 1.0 mM EDTA solution (198 mL of 0.7% saline and 2 mL of 100 mM EDTA) (for a total of 200 mL).

The solution was extracted at 50° C., spun, filtered, and thimerosal (0.14 g/L) was added. Testing was done using a glycine (4.6%) and calcium chloride (16 mM) solution: one part extract, three parts $Ca^{2+}$/glycine solution.

Tests revealed the following prothrombin time (PT) values.

Using normal control plasma (Helena Laboratories, Norm-Trol): 10.7 secs, 10.8 secs, 10.1 secs and 10.2 secs.

Using abnormal control plasma missing calcium-dependent Factors II, VII, IX and X (Helena Laboratories, Ab-Trol I): 17.0 secs and 17.4 secs.

Comparative Example 2

A thromboplastin reagent was prepared from the same commercially available rabbit brain powder in Example 1 according to the following process:

A 10.0 g amount of rabbit brain powder was extracted using 0.7% saline (for a total of 200 mL).

The solution was extracted at 50° C., spun, filtered and thimerosal added (0.14 g/L). Testing was done using a glycine (4.6%) and calcium chloride (16 mM) solution: one part extract, three parts $Ca^{2+}$/glycine solution.

Tests revealed the following prothrombin time (PT) values.

Using normal control plasma (Helena Laboratories, Norm-Trol): 12.2 secs and 12.5 secs.

Using abnormal control plasma missing calcium-dependent Factors II, VII, IX and X (Helena Laboratories, Ab-Trol I): 20.1 secs and 20.9 secs.

As the above examples show, the process according to the invention in Example 1 using EDTA provides an unexpected improvement over the process in Comparative Example 2 not using EDTA.

In the above examples, prothrombin time (PT) was determined according to the following procedure.

Using the Helena Dataclot-2 of Helena Laboratories, which is an electro-mechanical coagulation instrument, PTs were performed with normal control plasma, (Helena Laboratories, Norm-Trol) and abnormal control plasma missing calcium-dependent Factors II, VII, IX, and X (Helena Laboratories, Ab-Trol I), and used the following volumes: 0.1 mL control plasma plus 0.2 mL thromboplastin reagent with calcium. The control plasma and the thromboplastin reagent with calcium were separately warmed to 37° C., then 0.2 mL of the thromboplastin reagent with calcium ions was pipetted into a reaction cup holding 0.1 mL of the control plasma, and the time required for clot formation was noted.

It will be understood that the above description of the present invention is susceptible to various modifications, changes and adaptations, and the same are intended to be comprehended within the meaning and range of equivalence of the appended claims.

We claim:

1. A process for preparing a thromboplastin reagent comprising:

providing an aqueous thromboplastin extract of a powdered thromboplastin source and a metal ion chelator; and mixing said thromboplastin extract with a source of calcium ions to provide a thromboplastin reagent.

2. The process for preparing a thromboplastin reagent according to claim 1, further comprising:

freeze drying said thromboplastin reagent.

3. The process for preparing a thromboplastin reagent according to claim 1, wherein said powdered thromboplastin source is rabbit brain powder.

4. The process for preparing a thromboplastin reagent according to claim 1, wherein said powdered thromboplastin source is powdered human placenta.

5. The process for preparing a thromboplastin reagent according to claim 1, further comprising:

mixing said thromboplastin reagent with a stabilizer.

6. The process for preparing a thromboplastin reagent according to claim 1, further comprising:

mixing said thromboplastin reagent with a preservative.

7. The process for preparing a thromboplastin reagent according to claim 1, wherein said metal ion chelator is selected from the group of ethylenediaminetetraacetic acid, ethylenebis(oxyethylenenitrilo)tetraacetic acid, and salts thereof.

8. The process for preparing a thromboplastin reagent according to claim 7, wherein said metal ion chelator is selected from the group consisting of ethylenediaminetetraacetic acid and salts thereof.

9. A process for preparing a thromboplastin extract comprising:

providing a powdered thromboplastin source comprising powdered human placenta;

extracting said powdered thromboplastin source in an aqueous solution comprising a metal ion chelator;

separating said powdered thromboplastin source in aqueous solution into sedimented powder and supernatant thromboplastin extract; and isolating said supernatant thromboplastin extract.

10. The process for preparing a thromboplastin extract according to claim 9, wherein said metal ion chelator is selected from the group consisting of ethylenediaminetetraacetic acid, ethylenebis(oxyethylenenitrilo)tetraacetic acid, and salts thereof.

11. The process for preparing a thromboplastin extract according to claim 10, wherein said metal ion chelator is selected from the group of ethylenediaminetetraacetic acid and salts thereof.

12. A process for preparing a thromboplastin reagent comprising:

preparing a supernatant thromboplastin extract according to claim 9; and mixing said supernatant thromboplastin extract with a source of calcium ions to provide a thromboplastin reagent with a metal ion chelator and calcium ions.

* * * * *